United States Patent [19]

Prunieras et al.

[11] Patent Number: 5,443,961
[45] Date of Patent: Aug. 22, 1995

[54] METHOD FOR DIAGNOSING CELLULAR AGING OR INFLAMMATION CONDITION OF KERATINOCYTES, AND KIT FOR IMPLEMENTING SUCH METHOD

[75] Inventors: Michel Prunieras; Michel Kermici; Francis Pruche, all of Paris, France

[73] Assignee: L'Oreal, Paris, France

[21] Appl. No.: 87,806

[22] PCT Filed: Jan. 16, 1992

[86] PCT No.: PCT/FR92/00034
§ 371 Date: Oct. 19, 1993
§ 102(e) Date: Oct. 19, 1993

[87] PCT Pub. No.: WO92/13098
PCT Pub. Date: Aug. 6, 1992

[30] Foreign Application Priority Data

Jan. 16, 1991 [FR] France ................... 91 00457

[51] Int. Cl.⁶ .............. C12Q 1/30; C12Q 1/26; C12Q 1/28; G01N 33/48
[52] U.S. Cl. ........................ 435/27; 435/25; 435/28; 436/63; 436/86; 436/904; 514/880
[58] Field of Search ............. 435/25, 27, 28; 424/7.1, 9, 2, 3; 514/880; 436/63, 86, 811, 904

[56] References Cited

U.S. PATENT DOCUMENTS 4,898,813  2/1990  Albarella et al. ................ 435/4

FOREIGN PATENT DOCUMENTS 0317070  5/1989  European Pat. Off. ............. 435/28

OTHER PUBLICATIONS

Aldrige "Hair Loss" Brit. Med. J. 289: 985–989 1984.
Yohn et al. "Disparate Antioxidant Enzyme Activities in Cultured Human Cutaneous Fibroblasts, Keratinocytes & Melanocytes" J. Invest Dermatol 97(3)405–409 Mar. 1991.
M. Kermici et al, "Evidence for an age-correlated change in glutathione metabolism enzyme activities in himan hair follicle", Mechanisms of Ageing and Development, vol. 53, No. 1, Mar. 1990, pp. 73–84.

Primary Examiner—Michael G. Wityshyn
Assistant Examiner—Nancy J. Degen
Attorney, Agent, or Firm—Cushman Darby & Cushman

[57] ABSTRACT

Method for diagnosing a cellular aging or inflammation condition of keratinocytes of the skin or a pilous follicle in a person, or for diagnosing the efficiency of a treatment intended to combat said condition. To this effect, the concentration or activity of certain markers (catalase, glutathion or glutathion peroxydase) is compared in the keratinocytes suspected of being pathological and the keratinocytes of a reference non pathological area. The pathological condition intensifies the activity of the catalase, or reduces the activity of other markers. Application particularly to the diagnosis of alopecia, and to the estimation of the efficiency of a treatment of baldness with minoxidil in a given individual.

17 Claims, No Drawings

METHOD FOR DIAGNOSING CELLULAR AGING OR INFLAMMATION CONDITION OF KERATINOCYTES, AND KIT FOR IMPLEMENTING SUCH METHOD

The present invention concerns a procedure for diagnosis of an inflammatory or cell-aging state in keratinocytes, or of the efficacy of a treatment designed to combat said cell aging or inflammation.

It is known that the epidermis is composed of cells called keratinocytes, which are continuously regenerated by division at the basal cell level and which become gradually differentiated and undergo modification so as to form a layer of keratinized cells, ultimately producing the stratum corneum, which consists of dead cells making up the outermost layer of the epidermis.

It is also known that hairs are produced in hair follicles formed from epithelial sheaths of epidermal origin and from a bulb (matrix) containing bulbar keratinocytes in a state of continuous division during the growth phases of the hair (anagenetic phase), these growth phases alternating with the resting phases, during which the hair ceases to grow and then "falls out" naturally. Following the natural loss of this hair, the underlying papilla forms a new hair follicle, and the cycle is repeated.

It has been observed, mainly in men, that in the zone forming the top of the skull (vertex), the hair-production cycles sometimes stop prematurely. This phenomenon is termed alopecia, which is not found in the peripheral areas of the skull, and, in particular, the back of the neck.

It is known that these alopecia phenomena are accompanied by various modifications of the keratinocytes of the hair follicle, in particular of the proportions of glutathione or glutathione peroxidase, which diminish in subjects in which the alopecia is well established (see, in particular, M. Kermici et al., IFSCC Congress, New York, October 1990).

It has now been discovered that these changes, which signify a state of cell aging, are already present in subjects not yet suffering from alopecia or who suffer from mild alopecia. The same is true for catalase activity (catalase being present in the keratinocytes of the hair follicles), which is increased in hair follicles located in the "alopecia zone" of subjects having alopecia or of those in whom is it latent.

By measuring the activity of these various markers of cell aging and by comparison with the proportion of these markers in hair follicle keratinocytes in zones not afflicted with alopecia (back of the neck), it is possible to detect pre-alopecia states making it possible to predict whether a given individual is liable to "lose his hair" prematurely.

It is known, moreover, that alopecia can be combatted, in particular by using minoxidil. However, treatment with minoxidil is not effective in some non-responding persons (about 40% of the cases treated).

Minoxidil causes, in particular, restoration of the equilibrium of the enzymatic activities between the hair follicles in the vertex and in the back of the neck. However, this restoration of balance is not observed in some subjects (responding subjects), while, in others (non-responding subjects), a restoration of this kind is not found.

These changes in enzymatic activity, especially in subjects predisposed to alopecia, can be reversed by treating with minoxidil, generally after approximately three to six months of activity.

However, it has been discovered that this desirable effect, i.e., the restoration, using minoxidil, of the balanced activity of glutathione peroxidase or of the concentration of glutathione in the hair follicles in the vertex area is possible only if this activity or concentration has not already been excessively disrupted prior to treatment, since, at that point, restoration of equilibrium using minoxidil can no longer be obtained. According, when the ratio of the concentrations or activities of these markers of aging in the zone tested and in the non-pathological control zone is greater or, depending on the case, lesser, than a certain threshold (which may be established by routine experiments), it then becomes possible using the invention procedure to determine whether treatment using minoxidil will be effective in a given individual.

With respect to catalase, on the other hand, minoxidil treatment will be effective when catalase activity is sufficiently intensified in the hair follicles of the vertex.

This opportunity for prediction is advantageous, since minoxidil treatments are long and costly.

Furthermore, it has been discovered that similar disruptions in the proportions of the various markers mentioned above are also present in skin keratinocytes in various pathological or pre-pathological and inflammatory conditions, or in cases of premature skin-cell aging not linked to a specific pathology. Here again, by comparing the proportion of cell-aging markers in the keratinocytes in the zone tested to the proportion in the keratinocytes sampled in a non-pathological area of skin, information is gathered which helps in diagnosing, and potentially prescribing, an appropriate treatment. The invention procedure also makes it possible to study the effects of this treatment.

In fact, this procedure makes it possible to determine whether this treatment will produce restored equilibrium of the proportions of markers in the treated skin patch.

It should further be observed that, in certain cases, the comparison of the proportions of markers in the keratinocytes in the area studied or treated can be compared with the average values recorded after preliminary analysis in a representative number of comparable individuals, who represent samples of the pathological and non-pathological populations.

The present invention thus concerns a procedure for diagnosis of the state of cell aging or of keratinocyte inflammation in an individual, or of the efficacy of a treatment designed to combat said aging or inflammation, characterized by the fact that, first, a sample of keratinocytes is taken in a pathologically-suspect area (i.e., an area which may suffer from a cell-aging or inflammatory condition) or in the treated area; that, second, keratinocytes are drawn from a non-pathological control area, or untreated zone; that, using conventional methods, the proportions of a marker of said cell-aging or inflammatory state are established in said keratinocytes; that said proportions in keratinocytes from the pathological area and those from a healthy or untreated zone are compared; and that said marker is selected among catalase, glutathione, and glutathione peroxidase, it being understood that increased catalase activity or reduction of the proportion of glutathione or of glutathione peroxidase activity in keratinocytes from the pathological, or untreated, area, as compared with the keratinocytes from the non-pathological, or untreated, area, constitutes the sign of an aging or inflammatory state or of the ineffectiveness of the treatment.

The expression "cell aging" generally signifies a process, sometimes reversible and sometimes irreversible, which, as a function of time and/or the number of cell divisions, produces a biological tissular or cellular modification such as, for example, reduced cell activity, mitotic incapacity (loss of the capacity for cell division), a loss of the ability to synthesize certain proteins, or the production of proteins (e.g., elastin) of poor quality. Cell aging may be induced or accelerated by the action produced by light, a phenomenon termed light aging.

The invention procedure may, of course, be used not only on keratinocytes taken from a skin sample, but also on skin cells cultivated in vitro.

According to one embodiment of the procedure, said keratinocytes are placed in contact with a predetermined quantity of hydrogen peroxide or hydroperoxide. Determination is made, using an appropriate tracer system, whether, after a predetermined period of time (at the end of which the tracer substance in contact with the keratinocytes from the control zone makes it possible to reveal the presence of hydrogen peroxide or hydroperoxide), the hydrogen peroxide or hydroperoxide is present, lacking, or reduced in the keratinocytes studied, it being understood that the absence of reduction of the hydrogen peroxide or hydroperoxide as compared with the keratinocytes from the control area is the sign of increased catalase activity, or vice versa.

According to a special embodiment, to determine catalase activity the keratinocytes are placed in contact with a tracer agent capable of becoming discolored by the hydrogen peroxide or by a hydroperoxide. A predetermined quantity of hydrogen peroxide or hydroperoxide, or of a hydrogen peroxide-generating system is added, and determination is made whether, at the end of the pre-determined time period, the tracer reagent remains colored, in which case catalase activity in the keratinocytes is increased in comparison with the keratinocytes from the control area, which is the sign of an inflammatory or cell-aging state or of the ineffectiveness of the treatment.

In particular, to determine catalase activity, said keratinocytes are placed in contact with a colored tracer agent capable of becoming discolored by the hydrogen peroxide, and with an oxidase and a substrate for said oxidase, and it is determined whether, after a pre-determined time at the end of which the reagent in contact with the non-pathological keratinocytes is discolored, the tracer reagent in contact with the keratinocytes tested remains colored, in which case catalase activity in the keratinocytes studied is increased, which is the sign of an inflammatory or cell-aging state, or of the ineffectiveness of the treatment.

The presence of catalase or of glutathione peroxidase in the biological medium may be controlled by immunological detection using specific antibodies, especially monoclonal antibodies. The disclosure of complexes formed in conjunction with these antibodies can be made using conventional immunological tracer methods or the system as described. As regards implementation of these immunological detection methods, mention may be made of YOCOTA, S and FAKIMI, H. D., "Immunocytochemical Localization of Catalase in Rat Liver," *J. Histochem. Cytochem.*, 29, 805–812 (1981), and J. A. LITWIN et al., "Immunocytochemical Localization of Peroxisomal Enzymes in Human Liver Biopsies," *American Journal of Pathology*, Vol. 128, No. 1 (July 1987).

The hydrogen peroxide-generating system can consist of any oxidase which produces hydrogen peroxide in the presence of an appropriate substrate (e.g., glucose in the case of glucose oxidase).

The oxidase may, for example, be glucose oxidase or cholesterol oxidase.

The tracer agent may consist, in particular, of a peroxidase and of a colored agent capable of becoming discolored by hydrogen peroxide or by a hydroperoxide in the presence of a peroxidase.

The colored agent may, for example, be 2,6-dichloroindophenol.

To determine glutathione peroxidase activity, said keratinocytes are placed in contact with a pre-determined quantity of hydrogen peroxide or of a hydroperoxide. Glutathione (reduced form), glutathione reductase, and its cofactor (NADPH) are added, and measurement is made of the quantity of NADPH consumed, which is proportional to glutathione peroxidase activity.

To determine the proportion of glutathione, the ground keratinocytes are placed in contact with an excess of an oxidizing agent capable of transforming glutathione in the reduced form into glutathione in the oxidized form, and with the glutathione reductase and its cofactor (NADPH). Measurement is made of either NADPH consumption or the transformed quantity of the reduced form of the oxidant.

In the glutathione-analysis procedure, the oxidizing agent is, for example, dithiobis-2-nitrobenzoic acid, whose reduced form is 5-thio-2-nitrobenzoic acid.

The keratinocytes studied may be those taken from the hair bulbs, in particular from the hair. According to this embodiment, the keratinocytes are gathered as hair follicles in the anagenetic phase (obtained by pulling out the hair).

In special embodiments:

the results obtained from a hair follicle sampled on an area of alopecia, or one which may become affected, and a hair follicle taken from an area which will not be affected by alopecia (back of neck).

the ratio r is calculated between catalase activity ($c_1$) in the follicle taken from the vertex and catalase activity ($c_2$) in the follicle taken from the back of the neck, and it is determined whether this ratio is greater than a predetermined value $r_1$, in which case, if r is greater than $r_1$, it is possible to predict that the treatment for alopecia using minoxidil on the subject examined will be effective, while it will be ineffective is r is less than $r_1$. The value of $r_1$ may be determined by routine experiments;

the ratio r' is calculated between the glutathione concentration of glutathione peroxidase activity ($c'_1$) in the follicle taken from the vertex and the glutathione concentration or glutathione peroxidase activity ($c'_2$) in the follicle taken from the back of the neck, and it is determined whether this ratio r' falls within an experimentally-determined range, in which case treatment of alopecia with minoxidil in the person examined will be effective, but ineffective in the contrary case.

The invention also concerns the materials needed for implementing the procedure described above. These materials are characterized by virtue of the fact that they comprise:

hydrogen peroxide, a hydroperoxide, means capable of producing hydrogen peroxide in situ, or an oxidizing agent capable of transforming glutathione in the reduced form into glutathione in the oxidized form, and/or a reducing agent (NADPH) capable of transforming glutathione in the oxidized form into glutathione in the reduced form;

means for determining the glutathione, glutathione peroxidase, or catalase proportion or activity;

and optionally, supports or containers for said sample.

In special embodiments, the required materials may be as follows, taken individually or, as required, in combinations:

The aforementioned means for producing hydrogen peroxide in situ include an oxidase;

Said means for determining catalase activity include a colored tracer reagent capable of becoming discolored by the hydrogen peroxide. This colored tracer reagent may contain a peroxidase and colored agent capable of being discolored by the hydrogen peroxide in the presence of a peroxidase. Said colored agent and said peroxidase may be deposited on said support as a polymer-material (e.g., gelatin)-based film. This film may also contain an oxidase.

These required materials may further contain, in a suitable container, a substrate for said oxidase;

They may also include, in suitable containers, glutathione, glutathione reductase, and NADPH;

Or these materials may include, in addition, in suitable containers, an oxidizing agent capable of transforming glutathione in the reduced form into glutathione in the oxidized form, glutathione reductase, and NADPH.

The methods used to obtain the results set forth above, which form the basis of the invention, will now be described.

ABBREVIATIONS

GSH: Glutathione
GSSG: Oxidized glutathione*
GSH-PX: Glutathione peroxidase*
GSSG-RD: Glutathione reductase*
H.F.: Hair Follicle * Enzymatic Activity

MATERIALS AND METHODS

Samples taken

Samples were taken from volunteers. After pulling out twenty hairs, observation under a binocular magnifier allowed selection of hair follicles in the anagenetic phase. Homogenization was carried out 24 hours after taking the samples in 100 μl of PBS Dulbecco buffer, pH=7.4. Activity levels were analyzed directly on the homogenate.

Measurements were made basically on cells from the outer epithelial sheath of the epidermis.

Measurement of Glutathione Peroxidase (GSH-PX).

10 μl of homogenate were diluted in 100 μl of buffer containing 10 mM $KH_2PO_4$, 1 mM EDTA, 1 mM $NAN_3$, 10 mM NaCl, and 5 mM glucose, pH=7.0.

30 μl of a mixture containing 0.2 mM NADPH, 1 mM GSH, and GSSG-RD in a proportion of 1 unit/ml were added.

After five minutes of preliminary incubation at 37° C., 30 μl of a solution of 0.25 mM tert-butyl-hydroperoxide or 0.09 mM $H_2O_2$ were added to trigger the reaction. Self-oxidation of the NADPH in the presence of tert-butyl-hydroperoxide was measured in parallel, using the method described by Paglia and Valentine, *J. Lab. Clin. Med.* (1967), 70, 158.

Measurement of Glutathione (oxidized and reduced)

On an aliquot of the homogenate, proteins were precipitated out using a 5% solution of 5-sulfosalicylic acid. After centrifugation, the GSH was measured using the enzymatic method of Griffith and Meister, *P.N.S.A. USA* (1979), 76, 268. The GSH was oxidized using 5,5'-dithiobis-2 nitrobenzoic acid (DTNB), with stoichiometric formation of 5-thio-2-nitrobenzoic acid (TNB). The oxidized glutathione was reduced in GSH specifically by glutathione reductase in the presence of NADPH. The formation of TNB was monitored by spectrophotometry at 412 nm, and was proportional to the total of the oxidized and reduced glutathione. Simultaneously, a range of GSH was measured under the same conditions (calibration). The results were expressed in GSH/gram of AND.

Measurement of AND using the DAPI (4-6-diamidino-2-phenylindole) Method

The AND-extraction method and measurement are described by Meyer and Grudman, *Arch. Dermatol. Res.* (1984), 276, 52. Measurement was carried out on 10 μl of sample, and the fluorescent AND-DAPI complex compound was analyzed with λ exc 360 nm and λ em 453 nm.

Catalase Measurement

This measurement was made according to the method described by Hugo Aebi in *Methods of Enzymatic Analysis*, Hans Ulrich Bergmeyer, ed., Verlag Chemie Internat., Deerfield Beach, Fla., Vol. 2, pp. 673-684 (1974).

Measurement of the reduction of $H_2O_2$ (pH: 7 at 25° C.) at 240 nm (activity expressed in μmoles $H_2O_2$ destroyed per minute and per μg of AND).

EXAMPLES OF TEST EXECUTION

A diagnostic kit was produced comprising:
a) a tracer system fixed in a gelatin base,
b) a reagent (glucose),
c) a reference scale adaptable to direct visual observation or an optical reading system (light meter, refractometer).

The tracer coloring agent system was 2-6 dichloroindophenol. This coloring agent was used at a concentration of 10 to 200 mg×l$^{-1}$.

The normal concentration is 16 mg/l in a gelatin solution in a phosphate buffer (pH=7.4).

The gelatin contained the following enzymes:
glucose oxidase (0.2 unit/ml)
horseradish peroxidase (0.16 unit/ml).

The gelatin-coloring agent-enzymes complex was spread on a glass slide and dried so as to obtain a homogeneous film.

The substrate of the glucose oxidase was glucose (0.50 g/liter).

Measurement was made in the following way:

Pulling a hair follicle out near the area of alopecia and/or pulling a hair follicle out in an area unaffected by alopecia (e.g., the back of the neck). The follicles selected were in the anagenetic phase.

The hair follicle was placed on the glass slide (or other support) containing the gelatin-enzyme film.

A drop of glucose solution (20 μl) was placed on the follicle and on another control area.

The reading was made after five minutes at ambient temperature (20°-25° C.).

The entirety of the control area became discolored. Discoloration was more or less inhibited at the root of the hair follicle.

In the simplest case, a reference to a blue scale and a graded size scale may be made by virtue of a magnification system.

The less significant the discoloration of the 2,6-dichloroindophenol, the greater the risk of alopecia.

In fact, the glucose oxidase/glucose system produced $H_2O_2$ in situ. The latter discolored the coloring agent (2,6-dichloroindophenol) in the presence of peroxidase. Through the high catalase activity, the hair follicle decomposed the $H_2O_2$ produced.

We claim:

1. A process for diagnosing a state of keratinocyte cell aging or of keratinocyte inflammation in an individual or for diagnosing the efficacy of a treatment designed to combat keratinocyte cell aging or keratinocyte inflammation, said process comprising:
   (a) taking a first sample of keratinocytes from a pathologically-suspect or treated area of an individual,
   (b) taking a second sample of keratinocytes from a non-pathological control or untreated area of said individual,
   (c) establishing the amount of a marker of said keratinocyte cell aging or keratinocyte inflammation in said first and second keratinocyte samples,
   (d) comparing the amount of said marker in said first and second keratinocyte samples, said marker being selected from the group consisting of catalase activity, glutathione activity and glutathione peroxidase activity,
   wherein a larger amount of catalase activity or a lesser amount of glutathione activity or glutathione peroxidase activity in said first sample as compared to the second sample indicate a keratinocyte inflammation or keratinocyte cell aging state or the ineffectiveness of said treatment.

2. The process according to claim 1, wherein establishment of said catalase activity further comprises
   separately placing the keratinocytes of said first and said second samples in contact with known amounts of hydrogen peroxide or hydroperoxide,
   measuring the variations of the amounts of hydrogen peroxide or hydroperoxide over time, and
   comparing said variations in said first sample and said second sample.

3. The process according to claim 2 comprising adding a tracer agent to said first and second samples of keratinocytes such that said measuring further comprises detecting a change in color of said tracer agent.

4. The process according to claim 1, wherein establishment of said catalase activity comprises contacting each of said first and second samples of keratinocytes with an oxidase and a substrate thereof for generating hydrogen peroxide in situ,
   measuring the variations of the amounts of hydrogen peroxide over time, and
   comparing said variations in said first and second samples.

5. The process according to claim 4 wherein said oxidase is glucose oxidase.

6. The process according to claim 4 comprising adding a tracer agent to said first and second samples of keratinocytes such that said measuring further comprises detecting a change in color of said tracer agent.

7. The process according to any one of claims 3 or 5 wherein said tracer agent is 2,6-dichloroindophenol.

8. A process according to claim 1 wherein establishment of said glutathione activity further comprises
   separately placing the keratinocytes of said first and said second samples in contact with an excess of an oxidizing agent which oxidizes glutathione from a reduced to an oxidized form to form separate mixtures,
   adding glutathione reductase and the reduced form of nicotinamide adenine dinucleotide phosphate (NADPH) to said separate mixtures, and
   measuring the amount of NADPH consumed in each mixture, or the amount of the reduced form of said oxidizing agent generated, said amount of NADPH consumed or of said reduced form generated being proportional to said glutathione peroxidase activity.

9. The process according to claim 8 wherein said oxidizing agent is dithobis-2-nitrobenzoic acid.

10. A process according to claim 1 wherein establishment of said glutathione peroxidase activity further comprises
    separately placing the keratinocytes of said first and said second samples in contact with predetermined quantities of hydrogen peroxide or hydroperoxide to form separate mixtures,
    adding glutathione in reduced form, glutathione reductase and NADPH to said separate mixtures, and
    measuring the amount of NADPH consumed in each mixture, said amount of NADPH consumed in each mixture being proportional to said glutathione peroxidase activity.

11. The process according to any of the claims 2 or 10 wherein said hydroperoxide is selected from the group consisting of tert-butyl hydroperoxide, cumene hydroperoxide, and a lipidic hydroperoxide present in said first and second keratinocyte samples.

12. The process according to claim 1 wherein said first sample of keratinocytes or said second sample of keratinocytes are derived from hair follicles in the anagenetic phase.

13. The process according to claim 1 wherein said first sample of keratinocytes is derived from a hair follicle contained in an area of alopecia or in a vertex and said second sample of keratinocytes is derived from a hair follicle contained in an area other than an area of alopecia or other than the vertex.

14. The process according to claim 13 wherein said second sample of keratinocyte is derived from a hair follicle from the back of the neck.

15. The process according to claim 14 further comprising
    calculating the ratio, r, between the catalase activity in said first sample of keratinocytes and the catalase activity in said second sample of keratinocytes, and
    comparing said ratio, r, to a predetermined ratio, $r_1$, such that when r is greater than $r_1$, minoxidil treatment will be effective for alopecia in the area from which said first sample of keratinocytes was derived.

16. The process according to claim 14 further comprising
    calculating the ratio, $c_1$, between the glutathione activity in said first sample of keratinocytes and the glutathione activity in said second sample of keratinocytes, and
    comparing said ratio to a predetermined range such that when said ratio, $c'_1$, is within said predetermined range, minoxidil treatment will be effective for alopecia in the area from which said first sample of keratinocytes was derived.

17. The process according to claim 14 further comprising
   calculating the ratio $c'_2$, between the glutathione oxidase activity in said first sample of keratinocytes and the glutathione oxidase activity in said second sample of keratinocytes, and
   comparing said ratio to a predetermined range such that when said ratio, $c'_2$, is within said predetermined range, minoxidil treatment will be effective for alopecia in the area from which said first sample of keratinocytes was derived.

* * * * *